United States Patent
Neumann et al.

(10) Patent No.: US 6,666,962 B2
(45) Date of Patent: Dec. 23, 2003

(54) ELECTROCHEMICAL SENSOR ELEMENT WITH A POROUS REFERENCE GAS ACCUMULATOR

(75) Inventors: Harald Neumann, Vaihingen (DE); Kurt Bayha, Oberriexingen (DE); Lothar Diehl, Stuttgart (DE)

(73) Assignee: Robert Bosch GmbH, Stuttgart (DE)

(*) Notice: Subject to any disclaimer, the term of this patent is extended or adjusted under 35 U.S.C. 154(b) by 43 days.

(21) Appl. No.: 09/445,631
(22) PCT Filed: Mar. 18, 1999
(86) PCT No.: PCT/DE99/00750
   § 371 (c)(1),
   (2), (4) Date: Mar. 31, 2000
(87) PCT Pub. No.: WO99/53302
   PCT Pub. Date: Oct. 21, 1999

(65) Prior Publication Data
US 2003/0136677 A1 Jul. 24, 2003

(30) Foreign Application Priority Data
Apr. 8, 1998 (DE) .................................. 198 15 700

(51) Int. Cl.[7] ............................................. G01N 27/407
(52) U.S. Cl. .......................... 204/427; 204/426; 204/429
(58) Field of Search ................................. 204/421–429

(56) References Cited

U.S. PATENT DOCUMENTS

| | | | |
|---|---|---|---|
| 4,502,939 A | * | 3/1985 | Holfelder et al. |
| 4,547,281 A | | 10/1985 | Wang et al. |
| 4,647,364 A | * | 3/1987 | Mase et al. .................. 204/425 |
| 4,900,425 A | * | 2/1990 | Sasayama et al. ........... 204/425 |
| 5,037,525 A | * | 8/1991 | Badwal ........................ 204/424 |
| 5,474,665 A | * | 12/1995 | Friese et al. ................ 204/426 |
| 5,494,557 A | * | 2/1996 | Hotzel et al. ................ 204/425 |
| 5,545,301 A | * | 8/1996 | Friese et al. ................ 204/425 |
| 5,630,920 A | * | 5/1997 | Friese et al. ................ 204/424 |
| 6,036,841 A | * | 3/2000 | Kato et al. ................... 204/426 |

FOREIGN PATENT DOCUMENTS

| | | |
|---|---|---|
| DE | 43 13 251 | 10/1994 |
| DE | 44 08 361 | 9/1995 |
| EP | 0 125 069 | 11/1984 |
| EP | 0 646 789 | 4/1995 |
| EP | 0 816 836 | 1/1998 |

OTHER PUBLICATIONS

F. Ephraim, "Inorganic Chemistry", 4th ed–rev., (1943) month unavailable, p. 429.*
Merriam–Webster's Collegiate Dictionary, 1998, (10th ed.), p. 553.*

* cited by examiner

*Primary Examiner*—T. Tung
(74) *Attorney, Agent, or Firm*—Kenyon & Kenyon

(57) ABSTRACT

An electrochemical sensor element, in particular for determining the oxygen level in gas mixtures, includes at least one measuring electrode exposed to a measured gas, at least one reference electrode exposed to a reference gas, at least one heating device, and one reference gas channel, through which the reference gas can be supplied to the reference electrode. The reference electrode is connected to the reference gas via a volume provided with pores. The volume is formed in a layer between the reference gas channel and the reference electrode.

9 Claims, 1 Drawing Sheet

ELECTROCHEMICAL SENSOR ELEMENT WITH A POROUS REFERENCE GAS ACCUMULATOR

FIELD OF THE INVENTION

The present invention relates to an electrochemical sensor element, in particular for determining the oxygen level in gas mixtures.

BACKGROUND INFORMATION

Sensor elements are known. They are designed as planar sensor elements, which have, on a solid electrolyte designed as a support, a first electrode exposed to the measured gas and a second gas exposed to a reference gas. Furthermore, an electrical resistance heater is embedded in the support. A reference gas, which is in most cases made up of atmospheric air, is supplied to the reference electrode via a reference gas channel integrated in the support. At the same time, the reference channel forms a gas chamber having a bottom surface matching the reference electrode in the reference electrode area, so that sufficient oxygen may reach the reference electrode.

It is known from European Patent No. 125069 that the width of the reference gas channel can be adapted to match the width of the electrode over its entire length for this purpose, or two reference gas channels, with one electrode arranged in each, can run in a layer plane parallel to one another, with the two electrodes connected together, forming the reference electrode. The disadvantage of a wide reference gas channel or a reference gas channel made up of two adjacent parts is that one part of the heating coil of the resistance heater element is always in the area of the perpendicular projection of the reference gas channel. This results in overheating of the solid electrolyte in the area of the reference gas channel. In addition, a wide reference gas channel provides poor heat transfer between the resistance heating element and the electrodes.

The method described in German Patent Application No. 19609323 in which the reference gas channel is branched in the area of the heating device, offers a possible remedy. However, in this case the reference electrodes must also be branched.

SUMMARY OF THE INVENTION

The sensor element according to the present invention has the advantage that it allows improved heat transfer between the electrodes and the resistance heating element, resulting in uniform heat distribution. The porous layer also helps relieve mechanical stresses that occur at the edges where the reference gas channel and the adjacent solid electrolyte film meet, and which may result in stress cracks in the ceramic support. In bridging a wide reference gas channel, the solid electrolyte film is bent, which results in additional mechanical stresses. Using the narrow reference gas channel, excessive bending of the adjacent solid electrolyte film is avoided. Furthermore, due to the large-surface contact of the reference electrode with the adjacent porous layer, better adhesion of the latter is achieved, since the reference electrode remains pressed between the adjacent films during lamination. This is also true for the lead to the reference electrode, with its resistance also being thereby reduced.

It should be emphasized that the reference gas channel may have a slightly widened handgrip shape in the area of the reference electrode. This allows oxygen exchange to be improved, in particular in the case of low pore volumes. The effect of the reference atmosphere can be intensified by adding an oxygen-storing material, for example, $CeO_2$, to the porous layer. This can be achieved by impregnating the porous layer or the porous electrode.

DETAILED DESCRIPTION

Figure 1:
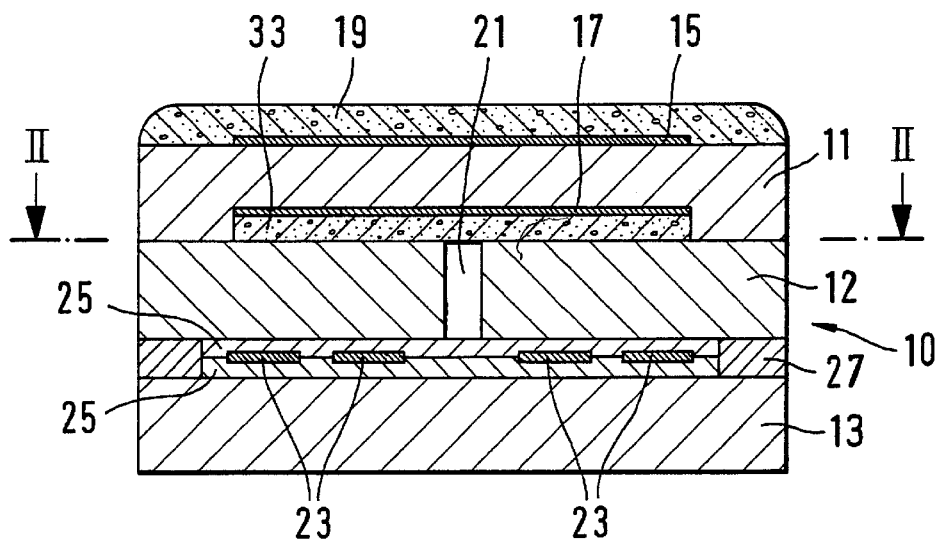
FIG. 1 shows a cross section through the sensitive part of a sensor element according to the present invention.

FIG. 1 shows a cross section through the measured gas side of a sensor element. The sensor element is a component of a gas sensor (not shown) and is secured in a housing of the sensor and its sensitive section is exposed to a gas to be measured. The sensor element is made of a ceramic support 10 having a planar layer structure with a first solid electrolyte film 11, a second solid electrolyte film 12, and a third solid electrolyte film 13 superimposed on one another. An outer large surface of first solid electrolyte film 11 has a measuring electrode 15 and its inner large surface has a reference electrode 17. Measuring electrode 15 is covered with a porous protective layer 19. Adjacent to first solid electrolyte film 11 is second solid electrolyte film 12, which has a narrow hollow cavity forming reference gas channel 21 in the middle. Between second solid electrolyte film 12 and third solid electrolyte film 13 an electrical resistance heating element 23 is arranged between two electrical insulating layers 25. Since electrical insulating layers 25 are porous so they can absorb mechanical stresses due to the different heat expansion coefficients of the materials used, a gas-tight solid electrolyte frame 27 is placed around insulating layer 25. Electrical resistance heating element 23 is designed as a heating coil on the sensitive section of the sensor element.

Figure 2:
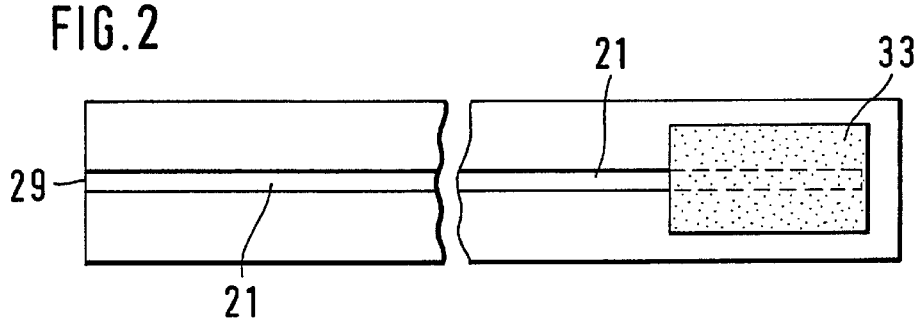
FIG. 2 shows a longitudinal section through the sensor element along line II—II of FIG. 1 according to a first embodiment.
Figure 3:
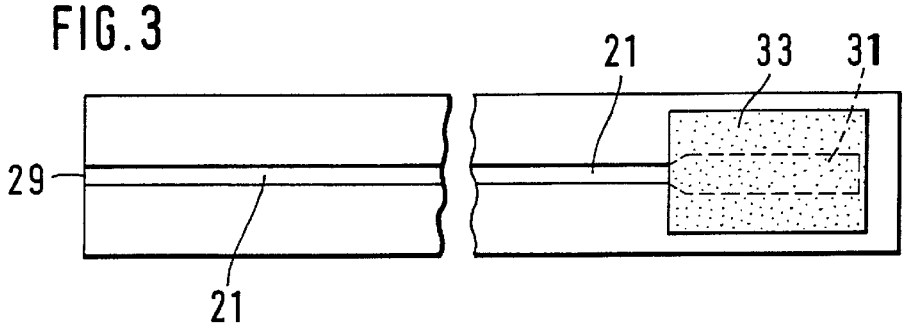
FIG. 3 shows a longitudinal section through the sensor element along line II—II of FIG. 1 according to a second embodiment.

On one narrow side of ceramic support 10, reference channel 21 has a reference gas opening 29 and runs approximately to the opposite end face of ceramic support 10, where reference gas channel 21 is closed. In the embodiment of FIG. 2, reference gas channel 21 has a uniform, for example, rectangular, cross section over its entire length. For example, the width of unsintered reference gas channel 21 is 0.4 mm to 0.8 mm, preferably 0.6 mm. The height of reference gas channel 21 is equal to the thickness of sintered solid electrolyte film 12, for example, 0.4 mm. In the embodiment of FIG. 3, reference gas channel 21 has a slightly widened section 31 in the area of reference electrode 17, so that reference gas channel 21 has a handgrip shape overall when viewed from above. Reference gas channel 21 may also branch off in the area of reference electrode 17.

Reference electrode 17, which has a flat shape in the plane of ceramic support 10, is covered with a porous layer 33 according to a first embodiment. Porous layer 33, which is represented by a dotted surface in FIGS. 2 and 3, is embedded between reference electrode 17 and the adjacent second solid electrolyte film 12. First solid electrolyte film 11 has a depression, for example, on whose bottom reference electrode 17 is placed with the porous layer filling the depression over reference electrode 17. Thus porous layer 33 spans reference gas channel 21 in this area after films 11, 12, 13 have been laminated together. The reference gas penetrating via reference gas opening 29 then diffuses via porous layer 33 to reference electrode 17 positioned thereon. The thickness of the porous layer is 5 $\mu$m to 200 $\mu$m, preferably 20 $\mu$m to 50 $\mu$m.

In another embodiment for performing gas exchange with the reference gas, reference electrode 17 itself has a porous design. Furthermore, an embodiment may use one porous layer and one porous reference electrode. A suitable pore volume is required in order to form an appropriate reference gas chamber. This is achieved through the thickness of porous layer 33 and/or of porous reference electrode 17.

Good oxygen exchange can be achieved at reference electrode 17 by adding an oxygen-storing material, for example, $CeO_2$, to porous layer 33 and/or porous reference electrode 17. The oxygen-storing material can be added by impregnating porous layer 33 and/or porous reference electrode 17.

If the sensor element is operated as a concentration cell, reference electrode 17 can be supplied with sufficient oxygen by applying an electric voltage to measuring electrode 15 and reference electrode 17. Thus an oxygen pumping effect is achieved in that oxygen is pumped from measuring electrode 15 to reference electrode 17. An additional pumped internal oxygen reference is thus formed on reference electrode 17.

What is claimed is:

1. An electrochemical sensor element for determining an oxygen level in a gas mixture, comprising:
    at least one measuring electrode exposed to a measured gas;
    at least one reference electrode exposed to a reference gas having an upper side proximate to the measuring electrode and a lower side distal to the measuring electrode;
    a porous layer containing a volume provided with pores, the layer being arranged adjacent to the lower side of the reference electrode such that the reference electrode is exposed to the reference gas via the layer; and
    a reference gas channel adjacent to the porous layer through which the reference gas is supplied to the reference electrode via the porous layer.

2. The sensor element according to claim 1, the layer defining a first volume and the reference gas channel defining a second volume.

3. The sensor element according to claim 1, further comprising an oxygen-storing material added to at least one of the layer and the reference electrode.

4. The sensor element according to claim 3, wherein the oxygen-storing material includes $CeO_2$.

5. The sensor element according to claim 1, wherein the measuring electrode and the reference electrode are connected as a concentration cell, an electrical voltage being applied to the measuring electrode and the reference electrode, resulting in an oxygen pumping effect from the measuring electrode to the reference electrode, a pumped internal oxygen reference being formed in the volume provided with pores.

6. An electrochemical sensor element for determining an oxygen level in a gas mixture, comprising:
    at least one measuring electrode exposed to a measured gas;
    at least one reference electrode exposed to a reference gas having an upper side proximate to the measuring electrode and a lower side distal to the measuring electrode;
    a layer containing a volume provided with pores, the layer being arranged adjacent to the lower side of the reference electrode such that the reference electrode is exposed to the reference gas via the layer; and
    a reference gas channel adjacent to the layer through which the reference gas is supplied to the reference electrode via the layer, the reference electrode oriented with a longitudinal axis parallel to a longitudinal axis of the reference gas channel, a width of the reference electrode perpendicular to the longitudinal axis of the reference electrode, a width of the reference gas channel perpendicular to the longitudinal axis of the reference gas channel, wherein the width of the reference electrode is greater than the width of the reference gas channel.

7. An electrochemical sensor element for determining an oxygen level in a gas mixture, comprising:
    at least one measuring electrode exposed to a measured gas;
    at least one reference electrode exposed to a reference gas having an upper side proximate to the measuring electrode and a lower side distal to the measuring electrode;
    at least one heating device;
    a layer containing a volume provided with pores, the layer being arranged adjacent to the lower side of the reference electrode such that the reference electrode is exposed to the reference gas via the layer; and
    a reference gas channel adjacent to the layer through which the reference gas is supplied to the reference electrode via the layer, wherein the reference gas channel is formed as a hollow space containing no porous material.

8. An electrochemical sensor element for determining an oxygen level in a gas mixture, comprising:
    at least one measuring electrode exposed to a measured gas;
    at least one porous reference electrode exposed to a reference gas having an upper side proximate to the measuring electrode and a lower side distal to the measuring electrode;
    at least one heating device;
    a layer containing a volume provided with pores, the layer being arranged adjacent to the lower side of the reference electrode such that the reference electrode is exposed to the reference gas via the layer; and
    a reference gas channel adjacent to the layer through which the reference gas is supplied to the porous reference electrode via the layer.

9. An electrochemical sensor element for determining an oxygen level in a gas mixture, comprising:
    at least one measuring electrode exposed to a measured gas;
    at least one reference electrode exposed to a reference gas having an upper side proximate to the measuring electrode and a lower side distal to the measuring electrode;
    a porous layer containing a volume provided with pores, the layer being arranged adjacent to the lower side of the reference electrode such that the reference electrode is exposed to the reference gas via the layer, the layer defining a first volume; and
    a reference gas channel adjacent to the porous layer through which the reference gas is supplied to the reference electrode via the porous layer, the reference gas channel defining a second volume, the second volume forming a hollow space containing no porous material.

* * * * *